United States Patent [19]

Cater

[11] 4,211,798

[45] Jul. 8, 1980

[54] PREPARATION OF PROTEIN ENRICHED YEAST PRODUCTS DEVOID OF CARBOHYDRATES

[75] Inventor: Allen W. Cater, Edina, Minn.

[73] Assignee: CRS Co., St. Paul, Minn.

[21] Appl. No.: 854,718

[22] Filed: Nov. 25, 1977

[51] Int. Cl.² .................. A23J 1/18; A23L 1/28; C12C 11/18
[52] U.S. Cl. ......................... 426/41; 426/60; 435/255; 435/256; 435/940
[58] Field of Search ............ 426/41, 60, 62, 583; 195/82; 435/255, 256, 940

[56] References Cited

U.S. PATENT DOCUMENTS

| | | | |
|---|---|---|---|
| 2,363,730 | 11/1944 | Hall | 426/41 |
| 2,809,113 | 10/1957 | Stimpson et al. | 426/41 |
| 3,818,109 | 6/1974 | Bechtle | 426/41 |
| 3,974,030 | 8/1976 | Kobayashi et al. | 426/60 X |

OTHER PUBLICATIONS

Webb, et al., By Products from Milk, 2nd ed., The Ari Publ. Co., Inc., Westport, Conn., 1970 (pp. 47–56).
Wasserman et al., Whey Utilization V. Growth of *Saccharomyces fragilis* in Whey in a Pilot Plant., J. Da. Sci., vol. 44, 1961 (pp. 387–392).

*Primary Examiner*—David M. Naff
*Attorney, Agent, or Firm*—Orrin M. Haugen; Thomas J. Nikolai

[57] ABSTRACT

The present invention concerns methods for producing food products consisting of highly nutritional proteins and yeast which are substantially devoid of objectionable carbohydrates. The process pertains to the addition of proteinaceous materials at appropriate stages of a yeast fermentation so as to enable the yeast to utilize the carbohydrate constituents of the protein material while recovering the protein with the yeast cells. These protein enriched yeast products are low in ash content with essentially no residual carbohydrates and are useful for fortifying foods and feeds.

3 Claims, 1 Drawing Figure

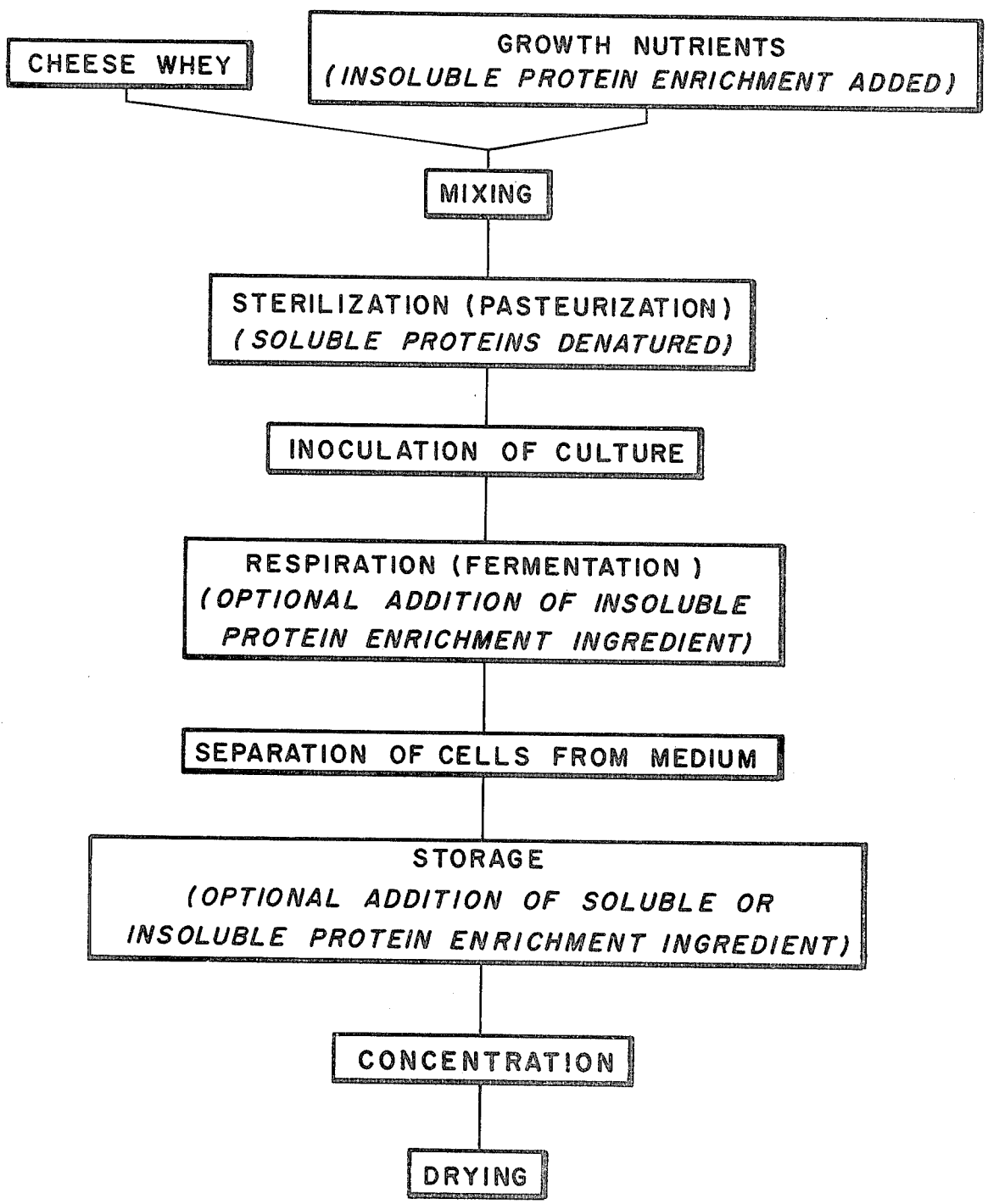
PROCESS-FLOW DIAGRAM

PREPARATION OF PROTEIN ENRICHED YEAST PRODUCTS DEVOID OF CARBOHYDRATES

BACKGROUND OF THE INVENTION

The present invention relates generally to an improved technique for the preparation of protein enriched yeast products, and more particularly to a method of producing such products from whey fermentation systems. The process of the present invention provides finished products which are high in protein content, low in ash and essentially free of carbohydrates, especially reducing sugars.

It is generally acknowledged that the world is entering an era of protein shortage. Accordingly, various techniques have been explored for the protein enrichment of food products both for human and animal consumption. Since the recognition of the fermentation process by Pasteur, considerable effort has been made to develop single cell protein systems to provide protein materials of high nutritional quality. Only modest gains have been made in accomplishing this goal due to the inherent limitations of the amino acid profiles of the various single cell protein. Bacteria are low in cystine and tryptophan, yeast are low in cystine and methionine, while algae are low in cystine, methionine and isoleucine content.

Of the various processes for producing single cell proteins, yeast is one of the more desirable microorganisms, since in most cases, proteins in the fermentation medium are either not utilized or only modestly utilized as a nutrient by the yeast. Consequently, a yeast fermentation is the process of choice in this invention, although the basic concept could be foreseeably applied with other microbial propagation processes where elimination of an undesirable constituent could be accomplished.

To maintain the protein quality of the enriched final product, cheese whey is the preferred fermentation substrate. There is currently over 30 billion pounds of liquid whey available annually in the United States of America and whey proteins are known for their exceptional nutritional quality. Whey from the manufacture of cheese contains most of the nutrients essential for yeast fermentation (respiration) and yeast products have already been shown to provide products with some applications in both foods for human consumption and for animal feeds.

Utilization of single cell protein products have been limited for a variety of reasons. Nucleic acid content must be restricted to less than 2 grams in the average dietary intake. The maximum protein content of single cell proteins is species specific in that bacteria may contain 47-87% protein; fungi (molds) 40%; yeast 50-54%; and algae only 40%. Cell walls and protein/ash ratios also reduce the amounts that can be used effectively in food systems, and these protein ingredients should additionally possess appropriate functional properties for promoting utilization. All of the essential amino acids must be present in adequate amounts to provide the desired quality for human and animal nutrition.

To overcome some of these impediments, the present practice includes blending microbial protein products with other ingredients. Milk, casein, caseinates, whey, modified whey, lactalbumin, soy concentrates and isolates, egg products, corn, wheat and other flours are typical of the ingredients used in these mixtures. However, an additional problem is encountered in that each of these ingredients contain varying amounts of carbohydrates. In particular, the milk or dairy products contribute the reducing sugar, lactose, to the blend and lactose intolerance is a problem in certain sectors. For certain animals and insects, lactose ingestion can result in growth retardation and even death. In the winter feeding of bees, for example, products containing lactose are considered lethal and cannot be used. In accordance with the present invention, however, residual carbohydrates are removed, and specifically residual lactose is removed from the finished product.

Another problem with residual carbohydrates in ingredients used in food product systems is the browning reaction due to the combination of reducing sugars with amino acids during heat treatments. Thus, a high protein content product devoid of reducing sugars can promote increased food utilization.

One system has partially satisfied the above parameters, wherein, in the fermentation of cheese whey, the whey portions (lactoglobulins) are coagulated (heat denatured) with these proteins being recovered with the yeast cells at the separation step. Even in this system (Mayer, B. M., 1970, Whey Fermentation. Proceedings Whey Utilization Conference, U.S.D.A.—ARS Publ. No. 76-36, p. 48), the yeast product contains only 57-60% protein. In accordance with the present procedure, however, higher protein contents are obtainable and, as previously indicated, residual carbohydrates are essentially removed.

In accordance with the present invention, therefore, the above limitations are essentially overcome. Any protein enriching substance may be added to the fermentation at an appropriate point in the process to allow removal (utilization by the cells) of the carbohydrates, while increasing the protein content and improving the amino acid balance of the final product. A wide variety of products are possible by this technique. Undenatured or denatured proteins, high protein/ash ratios and functional properties may be altered to satisfy specific requirements for use.

SUMMARY OF THE INVENTION

Therefore, in accordance with this invention, microbial cells (yeast) are grown under conditions favoring respiration such that a proteinaceous ingredient is added at a stage in the process, such as just after separation of the cells (usually by centrifugation) and storage. Specifically, a respiration formulation is prepared and the respiration operation is promoted until the operation is substantially complete, it being important, however, that certain active cells remain. Thereafter, a protein enriching ingredient, either soluble or insoluble, is added to the cell slurry after separation of most of the cells from the respiration or fermentation medium. These operations occur prior to further concentration and drying to allow utilization of any carbohydrates which may be present in the enriching medium, (more particularly lactose and lactic acid) with the resultant product being high in protein, low in ash content and negligible in carbohydrate concentration.

It is understood that this is a respiration process primarily wherein sugar is oxidized to carbon dioxide and cell substance. This is in contrast to a fermentation process wherein sugar is converted to alcohol and carbon dioxide. The basic respiration process follows the procedures described by A. E. Wasserman ("The Rapid Conversion of Whey to Yeast", Dairy Eng., 1960, 77:374). This, as well as other respiration or fermentation processes, may be employed.

Although the process of the present invention is applicable to microorganisms of all types, the lactose respiring yeasts are of major interest. Klyveromyces (Saccharomyces) fragilis or K. lactis are particularly suitable for propagation in cheese whey media.

While this invention is applicable to batch systems, it is readily adaptable to continuous respiration (fermentation) systems. The whey proteins (lactoglobulins) may be denatured prior to inoculation of the yeast to the growth medium and additional insoluble or denatured protein ingredients may be added at this stage. Alternatively, during the fermentation, insoluble or denatured proteinaceous substances may be added as supplementation. Following separation (centrifugation) of the cells and insoluble protein matter, either soluble and/or insoluble protein ingredients may also be added. At any of the three stages mentioned, the protein enriching ingredient or combination may be added with the ultimate effect of producing the characteristics desired. The respiration (fermentation) is completed once all the carbohydrate is consumed and the separated slurry is concentrated further and dried by conventional means.

Other and further objects of the present invention may become apparent to those skilled in the art upon a study of the following specification, appended claims, and accompanying drawing.

BRIEF DESCRIPTION OF THE DRAWING

The FIGURE is a flow diagram illustrating the major operations involved in the method of producing protein enriched yeast products with the points of protein ingredient addition as related to the present invention.

DESCRIPTION OF THE PREFERRED EMBODIMENT

Various procedures for fermentation or respiration of microbial cells are well known to those skilled in the art and the present invention may be incorporated into any of these systems to improve the nutritional and functional properties of these single cell protein products. The yeast production processes of basic concern in this invention have been ably described by P. Vananuvat and J. E. Kinsella ("Production of Yeast Protein from Crude Lactose", J. of Food Sci., 1975, 40, 336–341); A. E. Wasserman, W. J. Hopkins and N. Parges ("Whey Utilization. Growth Conditions for S. fragilis", Sewage and Ind. Wastes, 1958, 30, 913–920) and numerous others.

In accordance with the preferred embodiment of the present invention, there are three stages in the yeast propagation system at which the protein enriching ingredient may be added. Dependent upon the amount of protein desired in the final product, a readily calculable amount of protein enriching ingredient can be added based upon the known amount of recoverable solids considered consistent with the particular propagation system.

As an example, the yeast solids recovery in a fermentation system normally produces 25 grams of solids for each liter of fluid whey. The yeast solids, on a dry (moisture-free) basis, contains 50% protein. To the fermentation is added 20 grams of the protein enriching ingredient which contains 90% protein. For simplicity, assume 100% recovery of the added protein ingredient which is normally realistically approached. Thus, 45 grams of product is obtained (25+20) containing 67.8% protein (50×25) plus (90×20). For example:

$$\frac{(50\% \text{ protein} \times 25 \text{ grams}) + (90\% \text{ protein} \times 20 \text{ grams})}{45 \text{ grams}} \times 100 =$$

67.8% protein (dry basis) product.

The following table shows some of the combinations which provide protein enriched yeast products with improved protein/ash ratios and substantially reduced lactose.

TABLE 1

| | | | Protein Percent | Ash Percent | Protein/Ash | Lactose Percent |
|---|---|---|---|---|---|---|
| A. | Washed whey grown yeast | | 55 | 10 | 5.5 | <0.2% |
| B. | Casein, Caseinates | | 91 (av.) | 3.35 (av.) | 27 | 0.6 (av.) |
| | % A | % B | | | | |
| | 50 | 50 | 73 | 6.7 | 10.9 | <0.2% |
| | 90 | 10 | 58.6 | 9.3 | 6.3 | <0.2% |
| | 10 | 90 | 87.4 | 4.0 | 21.9 | <0.2% |
| C. | Lactalbumin | | 80 | 2.5 (av.) | 32 | 5.5 (av.) |
| | % A | % C | | | | |
| | 50 | 50 | 67.5 | 6.2 | 10.9 | <0.2% |
| | 90 | 10 | 57.5 | 9.1 | 6.3 | <0.2% |
| D. | Whey Protein Concentrate | | 35 | 2.4 | 14.6 | 56.6 |
| | % A | % D | | | | |
| | 50 | 50 | 70 (1) | 6.4 | 10.9 | <0.2% |

(1) Lactose conversion to yeast protein is about 45%. In the A/D (50:50) product, 45% of the 56.6% lactose will contribute an additional 25% protein. Thus, 25% protein from ingredients lactose plus 45% protein from the protein constitutents of a and D give 70% protein.
(2) All values are calculated on a dry, moisture-free basis. Protein levels shown would be somewhat lower when the nitrogen analysis factor is 6.25 instead of 6.38. Kjeldahl nitrogen analysis factors: Nitrogen 33 0 6.25 for yeast protein; Nitrogen × 6.38 for milk proteins.

Selection of the particular protein enriching ingredient and amount to add is important when a specific amino acid profile or functional property is desired in the final product. If a higher level of the essential amino acid, leucine, is required in the final product, a caseinate is used, or to increase the phenylalanine content, egg albumin may be added (the carbohydrate, glucose, would be consumed in the fermentation). Therefore, the protein efficiency ratios of single cell proteins can be dramatically improved. Recognition of the contribution of B complex vitamins from the yeast portion of the product should also be considered in the determination of total nutritional quality of the product.

In accordance with the teachings of this invention, there is the option to add soluble or insoluble (denatured) proteinaceous ingredients such that the functional properties (e.g. emulsification, gellation, water binding, etc.) are enhanced. The only precaution is that only insoluble (denatured) proteins should be added at the beginning or during the actual fermentation, so that they are readily recovered later. Soluble proteins may be appropriately added following the general separation of the yeast cells from the fermentation medium, since they will not be lost and the carbohydrate will still be consumed during storage of the separated yeast cell slurry prior to final concentration and drying.

In order to better comprehend the various features of the present invention, the following specific example showing the preferred embodiment of the present invention is given:

EXAMPLE I

Cheese whey is gathered and maintained in a storage vessel and steam is injected until a temperature of 93° C. is achieved and maintained for approximately 25 minutes. This achieves precipitation of the whey proteins, with the cheese whey initially containing between 6% and 6.5% solids, and with the solids containing approximately 12% protein. Nutrients are added prior to precipitation of the whey proteins, with 0.5% dibasic potassium phosphate and brewer's yeast extract in an amount of 10 grams (0.1%) per liter of cheese whey.

Thereafter, Klyveromyces (Saccharomyces) is added at approximately $5 \times 10^8$ cells per ml. of cheese whey, and following inoculation, the temperature of the slurry is maintained at approximately 30° C., with ammonia and air being pumped into the slurry to promote fermentation. In order to provide the quantity of ammonia necessary, ammonium sulfate in a quantity to produce a concentration of 0.5 mols per liter. Also, oxygen in the form of air is passed through the medium to maintain the oxygen content at a level of about 5 mM oxygen. During this respiration operation, the lactose and lactic acid are essentially consumed with the total consumption occurring in approximately 8 hours. Prior to the completion of the respiration operation, 6 hours after inoculation, respiration is substantially 90% complete. The pH of the slurry is maintained at approximately 5.7 with sulfuric acid being added as required. In the event the pH drops below approximately 6.5, the pH level may be corrected by pumping in ammonia gas, or a suitable water soluble base such as sodium hydroxide may also be utilized. At the 8-hour point, the cells are separated from the slurry medium through a centrifuge, with approximately 95% of the cells being removed, the effluent being discarded as a liquid fertilizer. This slurry medium with the cells is transferred from the centrifuge to a storage vessel at which time an additional quantity of dried milk solids in an amount of 20 grams per liter of centrifuged slurry medium (15% total solids), with the material then being maintained in the storage vessel at a temperature of approximately 30° C. to aeration until respiration is completed. During this second phase of the respiration operation, the carbohydrate content due essentially to the reducing sugar lactose is substantially entirely consumed and converted to protein. Also, at this point the protein/ash ratio has reached approximately 87:4.

Following completion of the second respiration operation, the slurry is pasteurized, concentrated and passed through a conventional dryer to an exit temperature below 40° C. until excess water is removed.

As has been shown, a fermentation (respiration) process is provided which enables the production of protein enriched products substantially devoid of carbohydrates. These products have a wide variety of application, especially as highly nutritional and functional food supplements for man, animals, and insects wherein there is low lactose tolerance or other problems related to the presence of carbohydrates.

It will be appreciated, of course, that conventional drying techniques are employed, with temperatures being controlled so as to avoid damage to the constituents of the final product. Drying conditions for protein enriched products are, of course, well known in the art and no unusual drying treatment is required.

With regard to the process flow diagram illustrated in the FIGURE, it will be seen that the cheese whey together with an insoluble protein enrichment ingredient are mixed together, and thereafter are sterilized, or optionally with the soluble proteins being denatured during the sterilization or pasteurization process. The culture is then inoculated, and this is followed by the respiration operation. Cells are separated from the medium, and thereafter the materials are stored prior to concentration and drying. It will be appreciated that the insoluble protein enrichment ingredient may be added at any suitable time, with suitable products being obtained with the addition of such an ingredient prior to final concentration drying as set forth in the flow diagram of the FIGURE, or as an alternative, in the respiration operation prior to completion thereof. When soluble protein enrichment ingredients are considered for addition to the treated material, such additions must be made during storage so as not to lose them in the effluent during centrifugal separation.

I claim:

1. The method of producing carbohydrate-free protein enriched yeast products from cheese whey including the steps of:
   (a) preparing a growth medium comprising cheese whey containing yeast growth nutrients;
   (b) heating said growth medium to a temperature of about 93° C. and maintaining said temperature for approximately 25 minutes to precipitate whey proteins;
   (c) adding yeast to the growth medium;
   (d) permitting the yeast to ferment at about 30° C. with aeration whereby lactose and lactic acid in the growth medium are essentially consumed by the yeast and converted into carbon dioxide and yeast cell substance;
   (e) subjecting the fermented growth medium from step (d) to a centrifugal operation to separate therefrom a slurry containing substantially all of the yeast cells;
   (f) adding to the slurry from step (e) a carbohydrate containing protein enriching ingredient;
   (g) permitting the yeast in the slurry from step (f) to undergo further fermentation at about 30° C. with aeration whereby the carbohydrate of the protein enriching ingredient is essentially consumed by the yeast and converted into carbon dioxide and yeast cell substance;
   (h) concentrating the slurry from step (g); and
   (i) drying the resultant concentrate to obtain said carbohydrate-free protein enriched yeast product.

2. The method of claim 1 wherein the yeast added in step (c) is *Klyveromyces* (Saccharomyces) *fragilis* and wherein the amount of yeast added is approximately $5 \times 10^8$ cells per ml. of cheese whey.

3. The method of claim 1 wherein fermentation in step (g) is continued until the protein/ash ratio in the slurry reaches approximately 87:4.

* * * * *